United States Patent
Mazilu

(10) Patent No.: US 7,203,604 B2
(45) Date of Patent: Apr. 10, 2007

(54) METHOD OF PREDICTING MECHANICAL BEHAVIOR OF POLYMERS

(75) Inventor: Nicolae Mazilu, Silver Lake, OH (US)

(73) Assignee: Bridgestone Firestone North American Tire, LLC, Nashville, TN (US)

( * ) Notice: Subject to any disclaimer, the term of this patent is extended or adjusted under 35 U.S.C. 154(b) by 45 days.

(21) Appl. No.: 11/065,522

(22) Filed: Feb. 23, 2005

(65) Prior Publication Data

US 2005/0188770 A1    Sep. 1, 2005

(51) Int. Cl.
*G06F 19/00*    (2006.01)

(52) U.S. Cl. .......................................... 702/42; 702/33

(58) Field of Classification Search ............... 702/42, 702/33
See application file for complete search history.

(56) References Cited

U.S. PATENT DOCUMENTS 6,631,647 B2 * 10/2003 Seale ........................... 73/789
6,925,416 B2 *  8/2005 Miyamoto et al. ........... 702/182

OTHER PUBLICATIONS

Horgan et al., "A description of arterial wall mechanics using limiting chain extensibility constructive models", Biomechan Model Mechanbiol 1 (2003) 251-266.
Beatty, "An Average-Stretch Full-Network Model for Rubber Elasticity", Journal of Elasticity 70: 65-86, 2003.
Krishnasawamy et al., "Damage Induced Stress-Softening in the Torsion, Extension and Inflation of a Cyclindrical Tube", Q.Jl Mech. Appl. Math (2001) 54 (2), 295-327.

Haward, "The application of non-Gaussian chain statistics to ultralow density polyethylenes and other thermoplastic elastomers", Polymer 40 (1999) 5821-5832.
Jarecki, Molecular orientation and stress in biaxially deformed polymers.II. Steady potential flow, Polymer 43 (2002) 4063-4071.
Johnson et al., "The Mullins Effect in Equibiaxial Extension and its Influence on the Inflation of a Balloon", Int. J. Engng. Sci. vol. 33, No. 2, pp. 223-245, 1995 (0020-7225(94)E0052-K).
Gundogan et al., "Non-Gaussian elasticity of swollen poly (N-isopropylacrylamide) gels at high charge densities", European Polymer Journal 39 (2003) 2209-2216.
Beatty et al., "A theory of stress-softening in incompressible isotropic materials", Journal of the Mechanics and Physics of Solids 48 (2000) 1931-1965.

(Continued)

*Primary Examiner*—Bryan Bui
*Assistant Examiner*—Douglas N Washburn
(74) *Attorney, Agent, or Firm*—Timothy Nauman; Thomas Kingsbury

(57) ABSTRACT

A method of determining performance characteristics and/or internal structural features of hyperelastic polymer materials includes performing at least one macro-level loading experiment on a sample comprised of a given composition. From the macro-level loading experiment, a set of internal structural features are determined. More particularly, tensile and compressive uniaxial loading data is collected and fit with a stress-strain function being a ratio of two polynomials. A curve fit analysis yields a set of coefficients relating the uniaxial loading data to the stress-strain function. From these coefficients, a set of statistical parameters are calculated, yielding information about internal microstructural features of the polymer composition, and therefore, performance characteristics of a part comprised of the given polymer composition.

22 Claims, 10 Drawing Sheets

OTHER PUBLICATIONS

Rivlin et al., Dead loading of a unit cube of compressible isotropic elastic material, Z. agnew. Math. Phys. 54 (2003) 954-963.

Zúniga et al., "Forced vibrations of a body supported by viscohyperelastic shear mountings", Journal of Engineering Mathematics 40: 333-353, 2001.

Horgan et al., A Molecule-Statistical Basis for the Gent Constitutive Model of Rubber Elasticity, Journal of Elasticity 68: 167-176, 2002.

Horgan et al., "Finite thermoelasticity with limiting chain extensibility", Journal of the Mechanics and Physics of Solids, 51 (2003) 1127-1146.

Jarecki et al., "Development of molecular orientation and stress in biaxially deformed polymers. I. Affine deformation in a solid state", Polymer 43 (2002) 2549-2559.

Krishnaswamy et al., "The Mullins effect in compressible solids", International Journal of Engineering Science 38 (2000) 1397-1414.

Perrin "Analytic stress-strain relationship for isotropic network model of rubber elasticity", C. R. Acad. Sci. Paris, t. 328, Série 11 b, p. 5-10, 2000, Méchanique des milieux continues/Continuum Mechanics.

Zúniga et al., "Stress-softening Effects in the Transverse Vibration of a Non-Gaussian Rubber String" Meccanica 38: 419-433, 2003.

Mazilu et al., "Constitutive Research with Abaqus", 17th Annual Abaqus Users Conference, Boston, MA, May 25-27, 2004.

Beatty, "The Mullins E*ect in the Transverse Vibration of a Non-Gaussian Rubber String" (Abstract), Univ. of Nebraska-Lincoln, Nebraska, Seminar Oct. 2003.

Fried, "An elementary molecular-statistical basis for the Mooney and Rivlin-Suanders theories of rubber elasticity", *Journal of the Mechanics and Physics of Solids*, vol. 50, No. 3, pp. 57-582 (2002).

Zúniga et al., "Constitutive equations for amended non-gaussian network models of rubber elasticity", *International Journal of Engineering Science*, vol. 40, N. 20, pp. 2265-2294 (2002).

Yeoh et al., "A New Attempt to Reconcile the Statistical and Phenomenological Theories of Rubber Elasticity",*Journal of Polymer Science Part B: Polymer Physics*, vol. 35, Issue 12, pp. 1919-1931, (Sep. 15, 1997).

* cited by examiner

METHOD OF PREDICTING MECHANICAL BEHAVIOR OF POLYMERS

BACKGROUND OF THE INVENTION

The present invention relates to a method of statistically characterizing structural features in polymers. It finds particular application in conjunction with predicting and/or characterizing the mechanical behavior of rubber, and will be described with particular reference thereto. It is to be appreciated, however, that the present invention is also applicable to predicting and/or characterizing the mechanical behavior of other hyperelastic solids.

Traditionally, polymer product or structure designs, such as, for example, for seals, gaskets, and tires, have been developed on the basis of prior experience, part prototyping, and extensive experimental testing. While this method ultimately leads to adequate product designs, it is extremely costly, both in time and money. Consequently, with the advent of such technologies, as, for example, nonlinear Finite Element Analysis (FEA) and the associated computing technology, the trial and error methods of experimental testing can be largely replaced.

Finite Element Analysis is a structural analysis tool in which any product or structure, such as a tire, is segmented into fine elements and analyzed using calculations by means of a computer nor other appropriate processor. FEA allows a polymer design engineer to look at the behavior of a particular product without the expensive manufacturing and testing that is typically required in many conventional polymer product design processes. Moreover, FEA eliminates the lengthy trial and error process in polymer product design and reduces tool costs. FEA is also capable of evaluating the effects of material changes on a given product configuration by understanding deformation and stress patterns within the product geometry.

However, the accuracy of FEA is largely dependent upon accurate characterization and/or modeling of the product's material properties and geometry. While the deformation-related properties of metals, which are most often subject to FEA, are typically modeled using linear stress-strain equations, polymers such as rubbers exhibit nonlinear stress-strain relations even for the relatively small deformations experienced during normal use. The nonlinearity of the stress-strain relations of these materials is their specific trait and extends over the entire range of deformation, which is extremely large if compared with that of metals. In other words, polymers are hyperelastic materials, which typically exhibit nonlinear constitutive behavior. This behavior is a consequence of their macro-molecular structure.

The statistical description of macro-molecular chain length in polymers, as typically applied to the study of polymer rheology, is isotropic Gaussian in nature. The Mooney-Rivlin linear model of hyperelasticity, for example, is known to relate to such a statistical description. The general validity of this statistical characterization, however, is not conclusively confirmed by experiments. Rather, experiments typically reveal a type of non-linear behavior for polymers, which is inconsistent with the idea of a Gaussian statistical description of the polymer chain length, which governs the rubber deformation. However, little is known beyond the Mooney-Rivlin connection between non-linear constitutive behavior of polymers and their statistical description.

The present invention contemplates a new and improved method for determining fundamental properties of rubbers based on the idea that the macromolecular chain statistics is directly reflected in fundamental properties. Consequently, we determine the microstructure of hyperelastic materials directly from macro-level physical experiments.

SUMMARY OF THE INVENTION

Accordingly, a need exists for a method to directly determine, characterize, and/or predict the characteristics of the internal statistics and structure of polymers and other rubber-like materials directly from macro-level loading experiments.

In accordance with one aspect of the invention, a method of determining internal structural features of a hyperelastic material includes performing at least one uniaxial loading test on a sample comprised of the hyperelastic material, where the uniaxial loading test yields uniaxial loading data. The uniaxial loading data is fit with a stress-strain function of the form:

$$\sigma = \lambda \frac{A\lambda^2 + B\lambda + C}{a\lambda^2 + b\lambda + c}$$

where $\sigma$ is a measure of the uniaxial loading on the sample, $\lambda$ is a measure of the strain on the sample, and A, B, C, a, b, and c are coefficients relating the stress-strain function to the uniaxial loading data. Values for the coefficients A, B, C, a, b, and c are determined by curve fitting experimental data. A set of statistical parameters $\alpha$, $\beta$, $\gamma$, $\alpha_1$, $\beta_1$, and $\gamma_1$ are computed to represent stress and strain by equations of the form:

$$\sigma = \alpha + \beta \tan(\gamma \psi) \text{ and } \lambda = \alpha_1 + \beta_1 \tan(\gamma_1 \phi).$$

A set of internal structural features of the hyperelastic material are determined from the statistical parameters.

In accord with another aspect of the present invention, a method of determining performance characteristics of a rubber part having a given composition includes performing at least one macro-level loading experiment on a sample comprised of the given composition. From the macro-level loading experiment, a set of internal structural features are determined, where the internal structural features are characterized by a set of coefficients A, B, C, a, b, and c. A finite element analysis is performed using the set of coefficients A, B, C, a, b, and c and a set of geometric configuration coefficients corresponding to the structure of the rubber part.

In accord with another aspect of the invention, a method of designing a polymer part having desired performance characteristics includes collecting the uniaxial loading data from a polymer sample having a first composition. The uniaxial loading data is fit with a stress-strain function having the form:

$$\sigma = \lambda \frac{A\lambda^2 + B\lambda + C}{a\lambda^2 + b\lambda + c}$$

where $\sigma$ is a measure of the uniaxial loading on the sample, $\lambda$ is a measure of the strain on the sample, and A, B, C, a, b, and c are coefficients relating the stress-strain function to the uniaxial loading data. Values are determined for the coefficients A, B, C, a, b, and c and a set of statistical parameters are computed based on these coefficients. The statistical parameters are related to the internal structural features of the polymer sample for which the uniaxial loading data is collected. At least one of the statistical parameters is modified in order to impose a second polymer composition. A plurality of coefficients A', B', C', a', b', and c' corresponding to the second polymer composition are calculated from the modified statistical parameters. A finite element structural analysis is performed on a polymer part having the second polymer composition to test performance characteristics.

In accord with a more limited aspect of the invention, the method further includes determining whether the polymer part having the second polymer composition exhibits the desired performance characteristics. If the polymer part does not exhibit the desired performance characteristics, at least one of the statistical parameters is again modified in order to impose a third polymer composition.

In accord with another aspect of the invention, a system for characterizing hyperelasticity of rubber-like materials includes means for collecting uniaxial loading data from a sample and means for fitting the uniaxial loading data with a stress-strain function which is a ratio of two polynomials. The system further includes means for determining values for a set of coefficients associated with the stress-strain function and means for computing a set of statistical parameters from the set of determined coefficients. In addition, the system includes means for deriving the internal structural properties of the rubber-like material from the computed statistical parameters.

Benefits of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
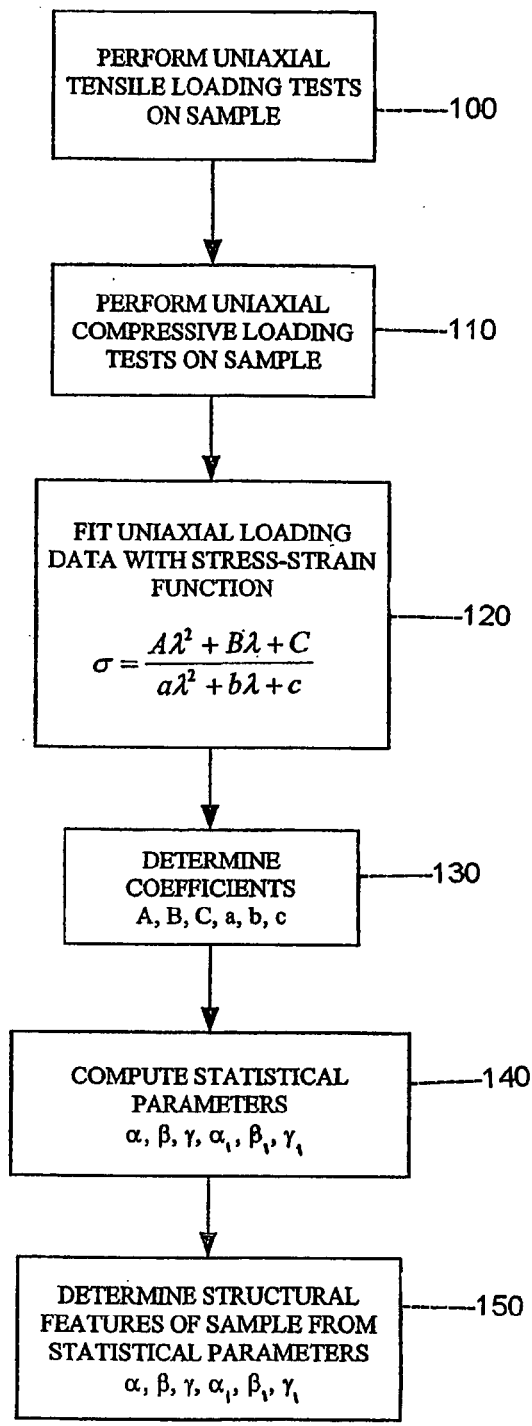
FIG. 1 is a flow chart illustrating a method of determining internal structural features of a rubber-like material in accord with the present invention.

As described more fully below, one embodiment of the invention includes a method of determining, characterizing or otherwise predicting internal structural or micro-structural features of hyperelastic solids directly from macro-level loading tests. As used herein, "hyperelastic" refers to materials that become stiffer at large deflections, that is, materials that yield a non-linear stress-strain curve. Hyperelastic solids include polymers and other rubber-like materials. In other words, the present invention develops and utilizes a link between micro-level quantification of internal structural features and macro-level performance for a given hyperelastic solid. The invention may find particular advantage in determining the characteristics of a tire tread rubber, comprised of SBR or natural rubber. Beneficially, the invention is capable of functioning on these traditional tire rubbers and can perform the evaluation notwithstanding the presence of other ingredients, such as fillers, antioxidants, colorants, vulcanizing agents, polymeric modifiers, etc.

Macro-level loading tests to evaluate deformation, such as pure shear and biaxial or uniaxial tensile and compressive loading tests, are performed on samples of known and unknown composition. The uniaxial loading data, i.e., the stress-strain data, is fit with a ratio of two quadratic polynomials to determine a set of regression coefficients. Further, a set of statistical parameters is calculated in terms of the regression coefficients. The statistical parameters reveal a set of micro-structural features for the rubber composition being analyzed.

From a theoretical point of view, stresses as well as strains, at a material point within a solid, can be represented with 3×3 matrices having special properties. When the stress or strain values are considered in all possible directions at the material point, the extreme values, i.e., local maxima or minima, are commonly referred to as the matrix eigenvalues. The matrix eigenvalues are the roots of a third degree equation having coefficients dependent upon the properties of the matrix in question. One such root may be written in the form $$\lambda = a + b \tan \phi \quad (1)$$

where a and b are real quantities and $\phi$ is an angle characterizing the orientation in a given plane in which the point where the matrix is calculated lies. The above form for eigenvalues is valid for both stress and strain. The term "experimental constitutive equations," as it is used herein, relates the eigenvalues of stress to the eigenvalues of strain, thereby describing material properties. The most natural of such relations are those coming directly from the algebraic form of the eigenvalues, and these are limited in number. If $\lambda$ from equation (1) is the experimental strain, the experimental stress may be represented by a relation like (1), namely:

$$\sigma = A + B \tan \psi \quad (2)$$

where A and B are matrix properties and $\psi$ is an angle characterizing the relationship between the given plane in which the material point lies and stress orientations. In this case, everything depends on the relation between $\theta$ and $\psi$.

In one case, where $\psi=\phi$, the stress is linear in strain and governed by $$\sigma = m\lambda + n \quad (3).$$

Artisans will appreciate that equation (3) provides a conventional small deformation approximation, where if n=0, the classical Hooke's law is provided.

In a second case, where $\psi=\phi+\phi_0$, the stress is homographic in strain i.e. a relation exists of the form $$\sigma = \frac{\alpha\lambda + \beta}{\gamma\lambda + \delta}. \quad (4)$$

This relation model has been shown to be valid for some soft biological tissues.

In a third case, where $\psi=2\phi$, the corresponding constitutive law is found to be $$\sigma = \frac{A\lambda^2 + B\lambda + C}{a\lambda^2 + b\lambda + c}. \quad (5)$$

It has been found that equation (5) is obeyed for a set of hyperelastic materials, such as polymers and the like.

A relation like equation (1) for stresses actually provides a resultant of forces acting in a solid. While it is thought to be nearly impossible to sum these forces, equation (2) can be viewed as a statistical mean over an ensemble of forces. Taken as such, it characterizes statistical distributions having the variance depending quadratically on their mean. It has been discovered that a relationship exists between these distributions and the internal structure or microstructure of the samples.

The idea is that, the most non-constraining probability distribution as obtained from experimental data in general is an exponential one: if X is the physical quantity to be measured, and $\theta$ is the measured value, then the distribution of the values $\xi$ of X is given by $$P_\theta(x) = \theta \cdot e^{-\theta\xi}. \quad (6)$$

Now, in real cases it may happen that X is not allowed to run on the whole real positive axis. This may be due to the fact that the real axis is already endowed with an apriori measure, or because of the fact that X has a limited range, which, from a mathematical point of view, comes to the same model. This model is represented by the following family of elementary probabilities depending on the experimental parameter $\theta$:

$$F_\theta(d\xi) = (N_m(\theta))^{-1} e^{-\theta\xi} m(d\xi), \quad (7)$$

where $m(d\xi)$ is the apriori measure of the real line, and the normalization factor is given by equation (8).

$$N_m(\theta) \equiv \int_{-\infty}^{\infty} e^{-\theta\xi} m(d\xi). \quad (8)$$

These probability distributions have the remarkable property, independent of the apriori measure $m(d\xi)$ of the real numbers, that their variance (VAR) can be related to their mean (x) by equation (9).

$$\text{VAR}(\xi) = \frac{dx(\theta)}{d\theta} \quad x(\theta) \equiv \int_{\text{Reals}} \xi \, dF_m(\xi) \quad (9)$$

$$\text{VAR}(\xi) \equiv \int_{\text{Reals}} \xi^2 \, dF_m(\xi) - \left(\int_{\text{Reals}} \xi \, dF_m(\xi)\right)^2.$$

A particular subclass of exponentials, with large applications in measurements is the family of distributions with quadratic variance function, for which the variance is a quadratic polynomial in the mean. For these exponentials the mean satisfies the differential equation $$\frac{dx(\theta)}{d\theta} = r_1 x^2 + 2r_2 x + r_3, \quad (10)$$

where $r_1$, $r_2$, $r_3$ are three real constants characterizing the distribution and are accessible to measurement.

However, "X" may not be a pure physical quantity considered subjectively, but a certain statistic of this quantity. For example, when measuring the coordinate in a vibration measurement, what may actually be measured is a squared statistic of this coordinate. It is known that the pressure between two bodies is measured as the contact force divided by the area of contact. Inside a body, the pressures are due to the attraction or repulsion of molecules and they are anisotropic, forming the stress matrix (or tensor, in more specific cases). It can be envisioned that the stress on a plane inside a body is a consequence of the resultant of forces between pairs of molecules formed of molecules situated on different sides of the plane. These pairs of molecules can be thought of as making a statistical ensemble, so the stress on the plane is to be taken basically as a mean force over that ensemble. In a simple tension experiment, it cannot be known exactly which plane contributes to the experimentally recorded stress and to what extent. However, it is known that an ensemble of ensembles of molecule pairs exist, each one of them characterizing a plane. Thus, the experimentally recorded stress can be considered a mean over this ensemble of ensembles. The speculations can go theoretically anywhere, but the logical chain must follow a pertinent observation: the stress as the eigenvalue of a 3×3 matrix has the functional form of the mean of a family of quadratic variance distribution functions. Indeed, solving the differential equation (10) we find, under condition $r_1 r_3 - r_2^2 > 0$ $$x(\theta) = -\frac{r_2}{r_1} + \frac{\sqrt{r_1 r_3 - r_2^2}}{r_1} \tan\left(\frac{r_1 \theta + r_2}{\sqrt{r_1 r_3 - r_2^2}}\right). \quad (11)$$

If now the parameter $\theta$ is taken as the angle of representation of stresses, equation (11) can be interpreted as the mean stress on a certain plane. This very plane is not so important by itself and, for experimental purposes, can be identified with a cross-sectional plane of the experimental specimen. Then the numbers $r_1$, $r_2$, $r_3$ or their counterparts in experimental records $$A \equiv -\frac{r_2}{r_1}; B \equiv \frac{\sqrt{r_1 r_3 - r_2^2}}{r_1}; \alpha \equiv \frac{r_1}{\sqrt{r_1 r_3 - r_2^2}}; \beta \equiv \frac{r_2}{\sqrt{r_1 r_3 - r_2^2}} \quad (12)$$

are certainly related to the internal molecular properties of the specimen. In the specific case of rubbers these properties are those of the macromolecular chains and filler dispersions.

With respect to the relationship between the parameter θ of the family of quadratic variance distribution functions and the experimental recording, engineering experience to date indicates that the angle of representation of the stresses is in direct connection with the progress of deformation. If the deformation is quantified by the experimental stretch λ, then there is a relationship between θ and λ. This relationship can be determined indirectly from a comparison with experimental data. This step being with the measure m (dξ) used for the characterization of the ideal continuum approximating the real body, and determine the measure that best fits experimental needs. These measures may not be always positive, but the fact remains that, no matter of this characteristic, they always give results in finite terms. In order to exemplify the polynomial measures are given in the following table.

| m(dξ) = dξ | $N_m(\theta) = \frac{1}{\theta}$ |
|---|---|
| m(dξ) = ξdξ | $N_m(\theta) = \frac{1}{\theta^2}$ |
| m(dξ) = ξ²dξ | $N_m(\theta) = \frac{2}{\theta^3}$ |
| m(dξ) = ξ³dξ | $N_m(\theta) = \frac{6}{\theta^4}$ |
| m(dξ) = ξ⁴dξ | $N_m(\theta) = \frac{24}{\theta^5}$ |
| m(dξ) = (aξ + b)dξ | $N_m(\theta) = \frac{a + b\theta}{\theta^2}$ |
| m(dξ) = (aξ² + 2bξ + c)dξ | $N_m(\theta) = \frac{c\theta^2 + 2b\theta + 2a}{\theta^3}$ |

The table offers the normalization factors as functions of θ. By the simple transformation $$\theta = \frac{1}{\lambda}, \quad (13)$$

these normalization factors can be reduced to experimental terms and applied to a real situation. This situation is represented by the last row of the table in terms of the physical parameter:

$$dF_m(x) = \frac{1}{\lambda(2a\lambda^2 + 2b\lambda + c)} e^{-\frac{x}{\lambda}}(ax^2 + 2bx + c)dx. \quad (14)$$

For this family of distributions the mean is $$\bar{x} = \lambda \frac{6a\lambda^2 + 4b\lambda + c}{2a\lambda^2 + 2b\lambda + c} \quad (15)$$

This mean can be cast into the form $$\bar{x} = A + B\lambda + \frac{C}{\lambda + \alpha} + \frac{D}{\lambda + \beta}, \quad (16)$$

more suitable for practical purposes. It turns out to be (almost) identically satisfied by experimental data on rubbers for all kinds of simple tension.

The parameters a, b, A, B from (1) and (2) and, implicitly A, B, C, a, b, and c from equation (5) should thus be considered as reflections of some statistic over the internal structure of materials. In the case of polymers, these statistics include, but are not limited to, molecular chain length, molecular segment orientations and lengths, cross-link density, material density, orientation of molecule, molecular shape, type of randomness, specific distribution of monomer content, and the like. However, when these statistics are taken into consideration instead of equation (5) we have $$\sigma = \lambda \frac{A\lambda^2 + B\lambda + C}{a\lambda^2 + b\lambda + c}$$

With reference now to the figures, provided for purposes of illustrating preferred embodiments of the invention and not for limiting the same, FIG. 1 shows a method of determining the internal structure of a rubber-like or hyperelastic material, which includes performing one or more uniaxial tensile loading tests 100 on a sample. More particularly, the uniaxial tensile loading tests 100 include loading a sample, such as a rubber band, having a given composition, with a progressively increasing load or stress. In one embodiment, the samples are tested using a mechanical testing system, such as is manufactured and sold by Instron®, which is suitable for performing tensile and compressive uniaxial loading tests.

Figure 2:
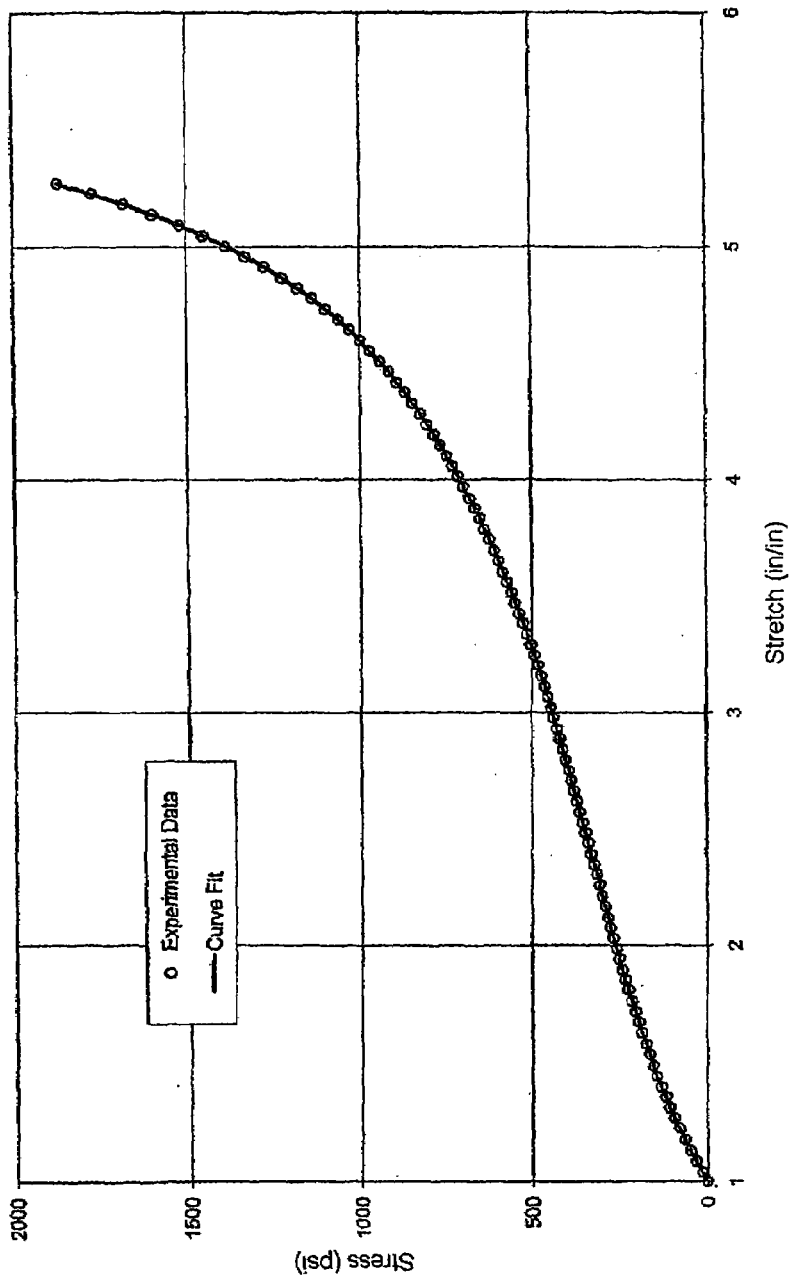
FIG. 2 is a plot for a first compound of uniaxial tensile stress vs. strain along with a curve fit that is collected in accord with the present invention.
Figure 3:
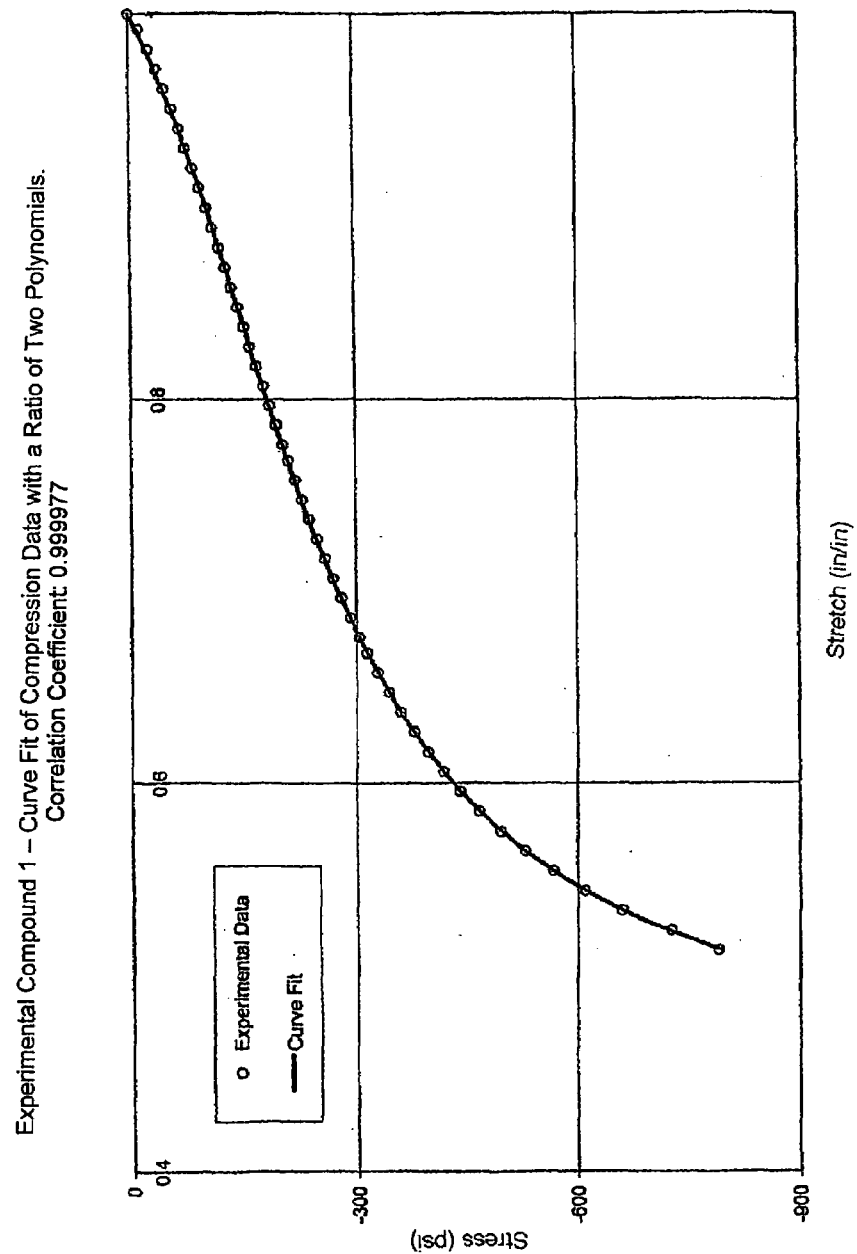
FIG. 3 is a plot for a first compound of uniaxial compressive stress vs. strain with a curve fit that is collected in accord with the present invention.
Figure 4:
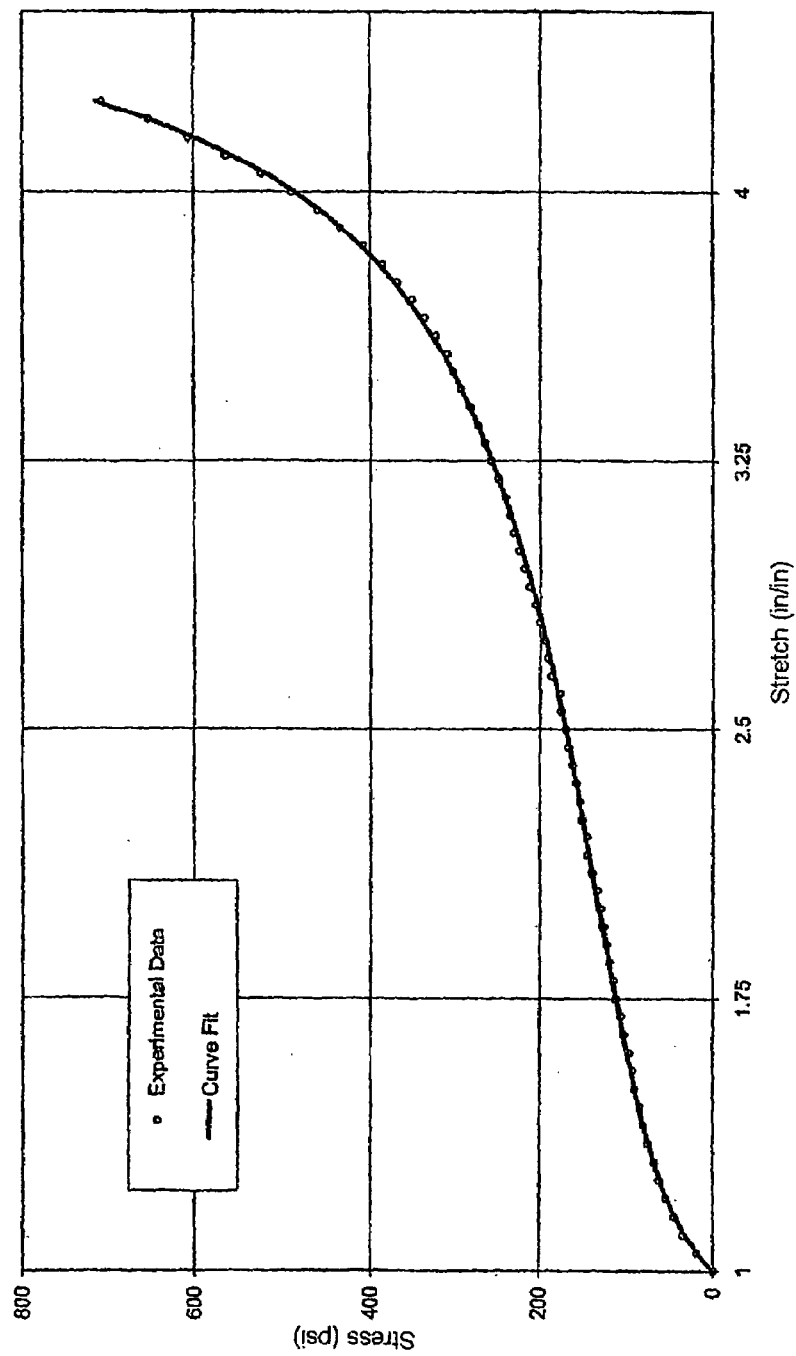
FIG. 4 is a plot for a second compound of uniaxial tensile stress vs. strain along with a curve fit that is collected in accord with the present invention.
Figure 5:
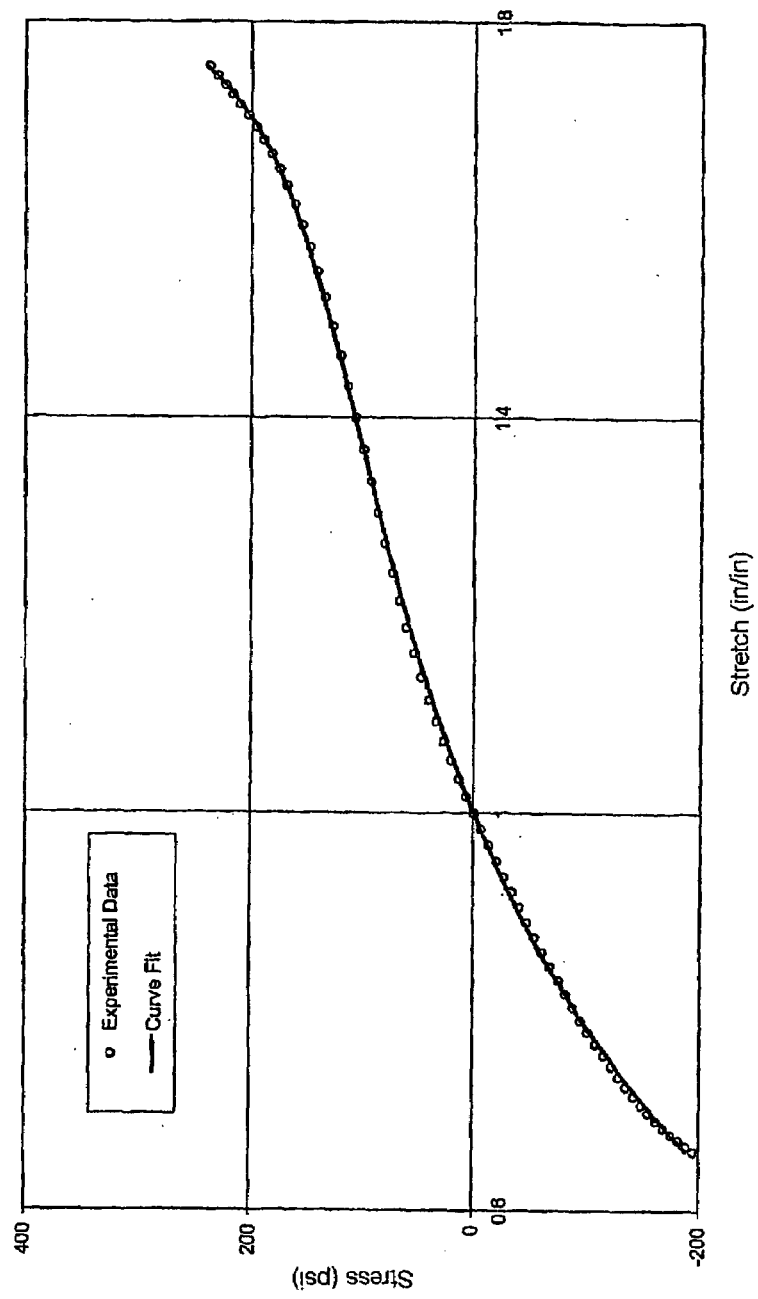
FIG. 5 is a plot for a third compound of uniaxial tensile stress vs. strain along with a curve fit that is collected in accord with the present invention.
Figure 10:
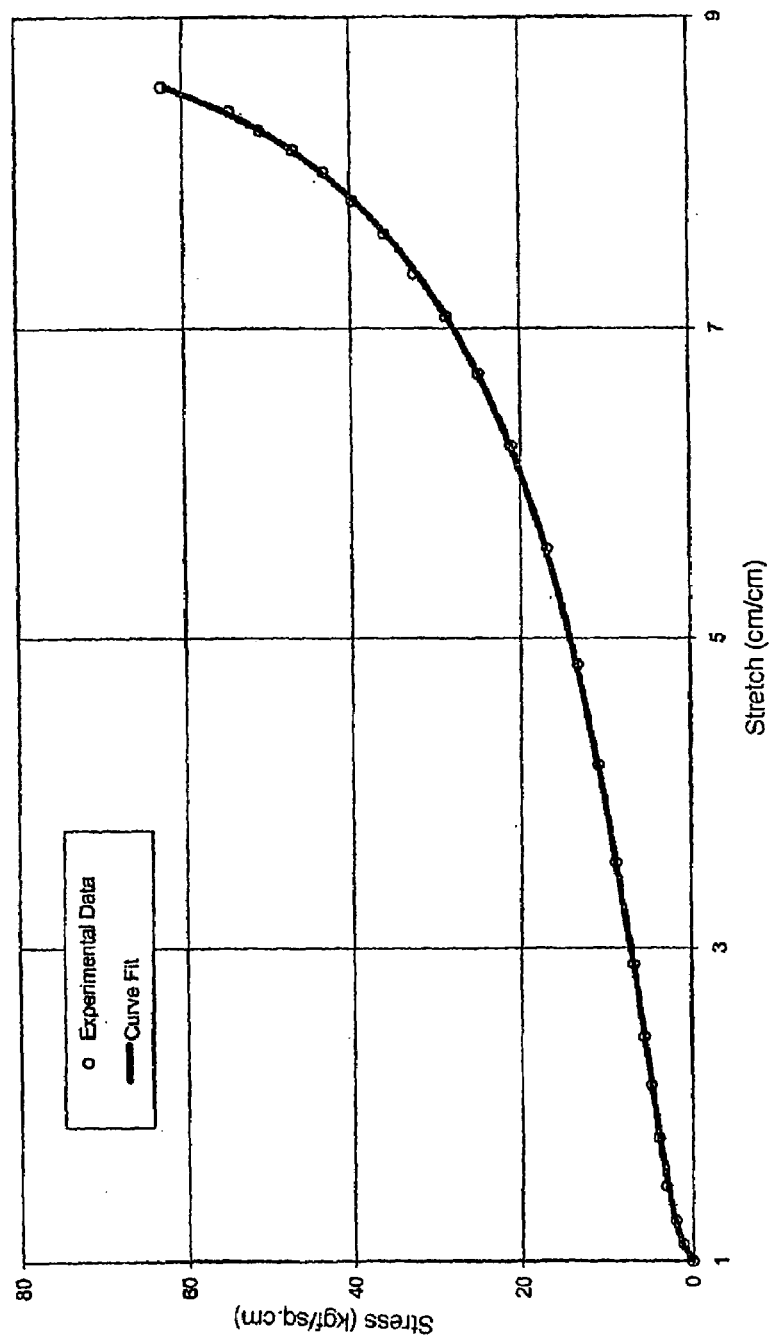
FIG. 10 is a plot for a compound of Treloar Data stress vs. strain along with a curve fit that is collected in accord with the present invention.

The deformation of a sample is recorded for a set of tensile loads and plotted, providing a stress-strain curve, as shown in FIGS. 2, 4 and 5. Similarly, a uniaxial compressive loading test 110 can be performed on a sample. As shown in FIG. 3, the relative compressive deformation of the sample is measured at a plurality of compressive loads or stresses, revealing a compressive stress-strain data set. It is to be appreciated that while the present invention is described in terms of uniaxial tensile and compressive loading tests, it is also amenable to the use of other loading tests such as equibiaxial, pure shear loading tests and Treloar Data (FIG. 10).

Preferably, the tensile and compressive stress-strain loading curves are fit 120 with a stress-strain function, which includes a ratio of two polynomials. The stress-strain function is of the form:

$$\sigma = \lambda \frac{A\lambda^2 + B\lambda + C}{a\lambda^2 + b\lambda + c} \quad (5)$$

where σ is a measure of the uniaxial loading or stress on the sample, λ is a measure of the stretch or strain of the sample, and A, B, C, a, b, and c are coefficients, i.e., regression coefficients, relating the stress-strain function to the experimentally-acquired uniaxial loading data illustrated in FIGS. 2–5. The values for the coefficients A, B, C, a, b, and c are determined 130 using conventional curve fit software and/or regression algorithms. More particularly, with reference to FIGS. 2–5, curve fitting the tensile and compressive loading data with a stress-strain function of the form provided in equation (5), yields an excellent fit and indicated in the respective correlation coefficients of r=0.99999; r=0.99998; r=0.99999; r=0.99999, respectively. As is described more fully below, the quality of the curve fit of the stress-strain function of equation (5), yields an extremely precise determination of coefficients A, B, C, a, b, and c, thus providing an accurate characterization of the micro-structural features of the material being tested. Once the stress-strain function coefficients A, B, C, a, b, and c are known, a set of statistical parameters are computed 140.

More particularly, statistical parameters $\alpha$, $\beta$, $\gamma$, $\alpha_1$, $\beta_1$, and $\gamma_1$ are computed 140 based on the stress-strain function having the form of equation (1) and equations of the form:

$$\sigma = \alpha + \beta \tan(\gamma\psi) \quad (6)$$

and $$\lambda = \alpha_1 + \beta_1 \tan(\gamma_1\phi) \quad (7).$$

In other words, the set of statistical parameters $\alpha$, $\beta$, $\gamma$, $\alpha_1$, $\beta_1$, and $\gamma_1$ are each calculated in terms of A, B, C, a, b, and c using equations (5), (6), and (7). Statistical interpretation of the statistical parameters $\alpha$, $\beta$, $\gamma$, $\alpha_1$, $\beta_1$, and $\gamma_1$ 150 yields the basic internal micro-structural features of the material being analyzed. More particularly, statistical parameters $\alpha$, $\beta$, $\gamma$, $\alpha_1$, $\beta_1$, and $\gamma_1$ are related to micro-structural features of the material, including, but not limited to, molecular chain length, molecular segment orientations and lengths, cross-link density, material density, orientation of molecule, molecular shape, type of randomness, specific distribution of monomer content, and the like.

Figure 6:
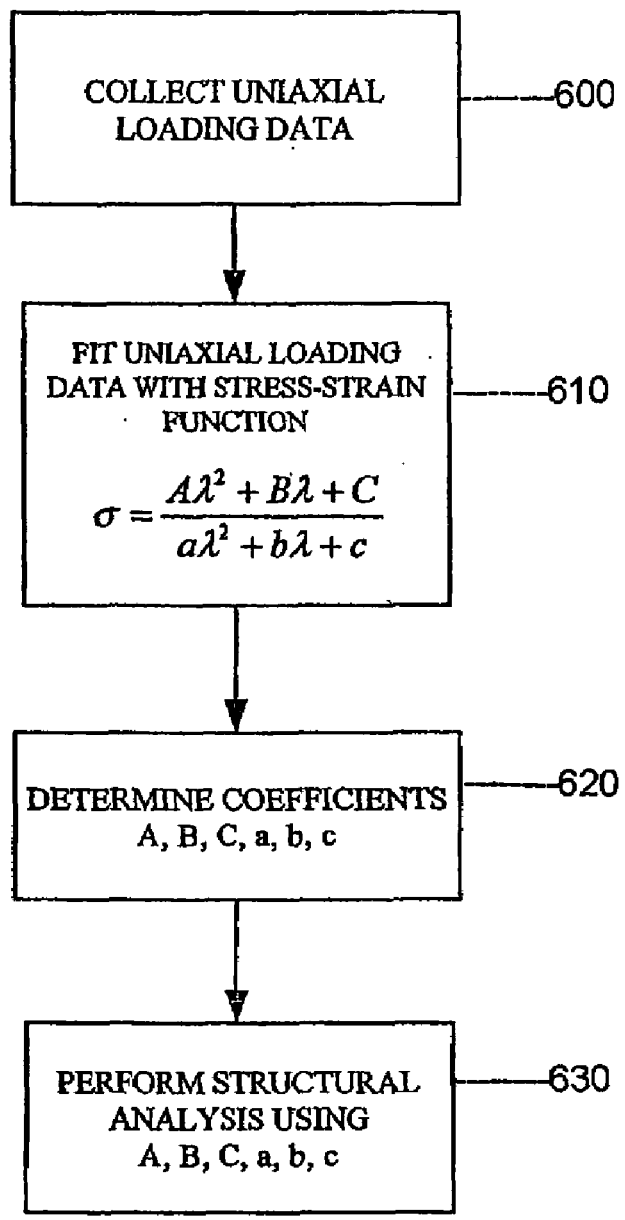
FIG. 6 is a flow chart illustrating a method of determining the performance of a given composition of rubber-like material in accord with the present invention.

With reference now to FIG. 6, a method of determining performance characteristics of a product or structure comprised of a rubber-like material includes collecting uniaxial loading data 600. As is described more fully above, a sample having a given, preferably a known, chemical composition is subject to one or more tensile and/or compressive loading experiments. The uniaxial loading data (illustrated, for example, in FIGS. 2 and 3) is fit with a stress-strain function 610, which includes a ratio of two polynomials. Preferably, as described above, the stress-strain function is of the form:

$$\sigma = \lambda \frac{A\lambda^2 + B\lambda + C}{a\lambda^2 + b\lambda + c} \quad (5)$$

where σ is a measure of the uniaxial loading or stress on the sample, and λ is a is a measure of the strain on the sample.

From the stress-strain relation, provided in equation (5) and the experimental uniaxial loading data, a plurality of coefficients A, B, C, a, b, and c 620 are determined using one of a variety of conventional curve fitting techniques, such as least squares fitting (illustrated, for example, in FIGS. 2–5). Once the coefficients A, B, C, a, b, and c have been determined 620, they are used to perform a theoretical structural analysis 630 on a part of the given composition. More particularly, the coefficients are input into Finite Element Analysis (FEA) software, along with other boundary conditions and geometric limitations. Artisans will appreciate that FEA software such as ABAQUS, is a tool used to determine performance characteristics of certain products or parts made of a material or a composition having well-known properties. By accurately fitting the uniaxial loading data with an appropriate stress-strain function and determining the coefficients A, B, C, a, b, and c, the performance characteristics of a given product, such as a tire, may be determined through FEA without performing actual physical tests.

For example, the performance characteristic of a tire, which is made from rubber having a known chemical composition or mixture of ingredients, may be tested using FEA software, rather than performing a series of costly and time-consuming physical laboratory tests. By performing uniaxial loading tests on a small sample of rubber having the same chemical composition as the tire to be tested and fitting the uniaxial loading data with the stress-strain function σ described above, A, B, C, a, b, and c will be determined and input into FEA software. The coefficients A, B, C, a, b, and c provide an accurate characterization of the hyperelasticity of the material of which the tire is comprised. Therefore, by adjusting boundary conditions and geometric parameters, simulations of a set of performance tests are performed using the FEA software.

Figure 7:
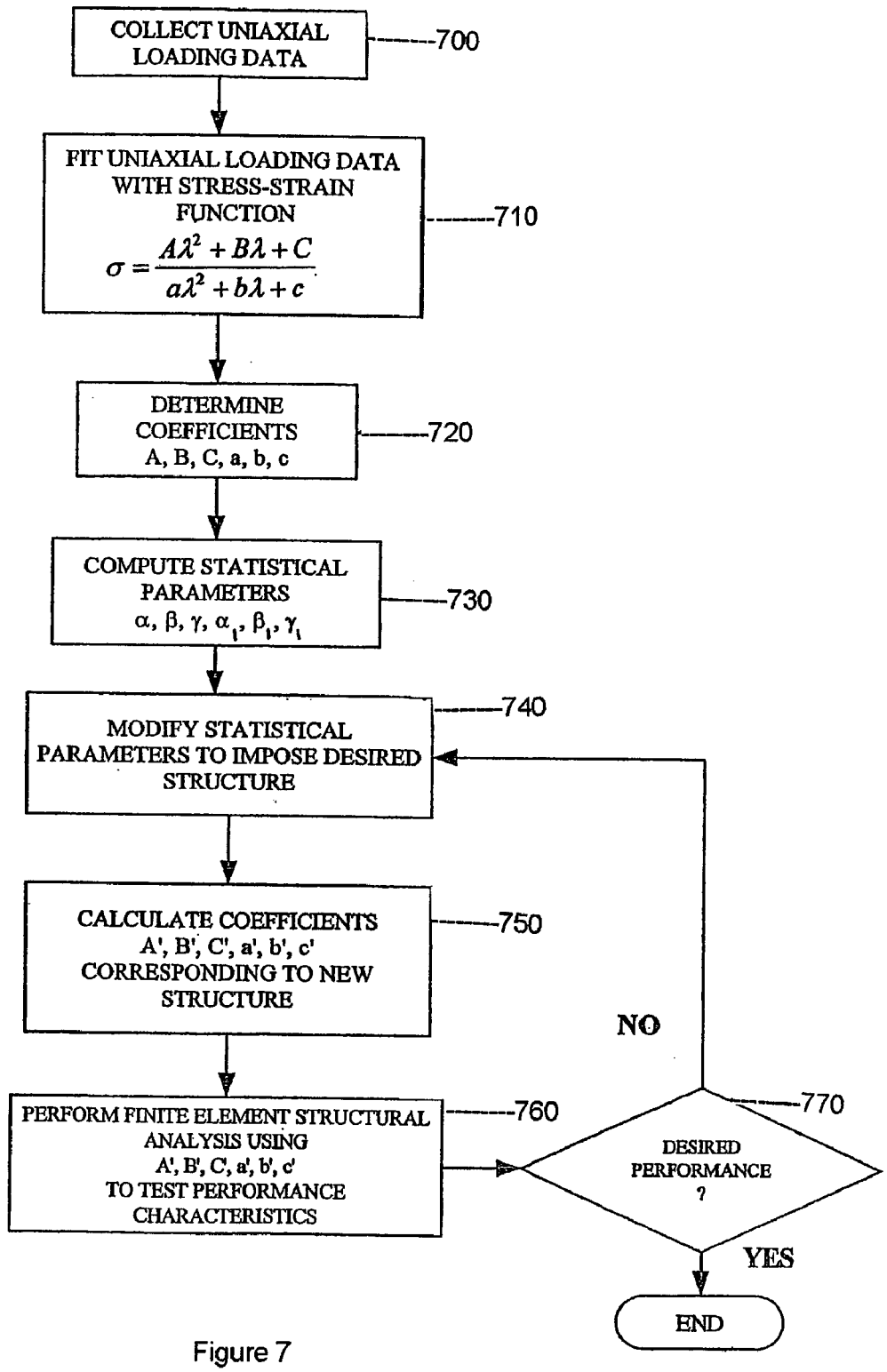
FIG. 7 is a flow chart illustrating a method of designing a rubber part having desired performance characteristics in accord with the present invention.

With reference to FIG. 7, a method of designing a rubber part having desired performance characteristics includes discovering the statistical nature of the internal structure of the rubber directly from the macro-level uniaxial loading experiments and determining the proper chemical composition so that the rubber in the desired product configuration corresponds to certain work or performance requirements. More particularly, tensile and/or compressive uniaxial loading data is collected 700 in the manner described above. The uniaxial loading data is fit with a stress-strain function 710 comprising a ratio of quadratic polynomials, preferably having the form:

$$\sigma = \lambda \frac{A\lambda^2 + B\lambda + C}{a\lambda^2 + b\lambda + c} \quad (5)$$

Using conventional curve fitting techniques described more fully above, the coefficients A, B, C, a, b, and c are determined 720.

A set of statistical parameters, $\alpha$, $\beta$, $\gamma$, $\alpha_1$, $\beta_1$, and $\gamma_1$, are calculated from the stress-strain function in equation (5) and equations of the form:

$$\sigma = \alpha + \beta \tan(\gamma\psi) \quad (2)$$

and $$\lambda = \alpha_1 + \beta_1 \tan(\gamma_1\phi) \quad (3).$$

As described above, the statistical parameters $\alpha$, $\beta$, $\gamma$, $\alpha_1$, $\beta_1$, and $\gamma_1$ reveal the internal micro-structural features of the initial rubber composition being tested. More particularly, statistical parameters $\alpha$, $\beta$, $\gamma$, $\alpha_1$, $\beta_1$, and $\gamma_1$ are related to micro-structural features of the material, including, but not limited to, molecular chain length, molecular segment orientations and lengths, cross-link density, material density, orientation of molecule, molecular shape, type of randomness, specific distribution of monomer content, and the like.

In an embodiment where the initial rubber composition in the desired geometric configuration does not exhibit the desired performance characteristics, one or more of the statistical parameters are modified 740. Modifying one or more of the above-referenced statistical parameters effectively serves to impose a second rubber composition having a second set of statistical parameters $\alpha$, $\beta$, $\gamma$, $\alpha_1$, $\beta_1$, and $\gamma_1$. Because the relationship between the statistical parameters and the coefficients A, B, C, a, b, and c are known due to the calculations in steps 710–730, an inverse calculation is performed 750 to yield the coefficients A', B', C', a', b', and c' corresponding to the second rubber composition.

The performance characteristics of a tire made from the second rubber composition are tested by inputting 760 the corresponding coefficients A', B', C', a', b', and c' into a FEA computer program. From the FEA computer simulation, it is determined 770 whether or not the desired performance characteristics are exhibited by the tire having the second or modified rubber composition characterized by $\alpha$, $\beta$, $\gamma$, $\alpha_1$, $\beta_1$, and $\gamma_1$. If the desired performance characteristics are present in the second rubber composition, the process is successfully terminated. If not, the statistical parameters are again modified 740 to impose a third desired structure corresponding to a third chemical composition, and the remaining steps are repeated. In addition, once a desired rubber composition is determined, the FEA software may be employed to test a variety of tire features, such as tread patterns and the like.

Figure 8:
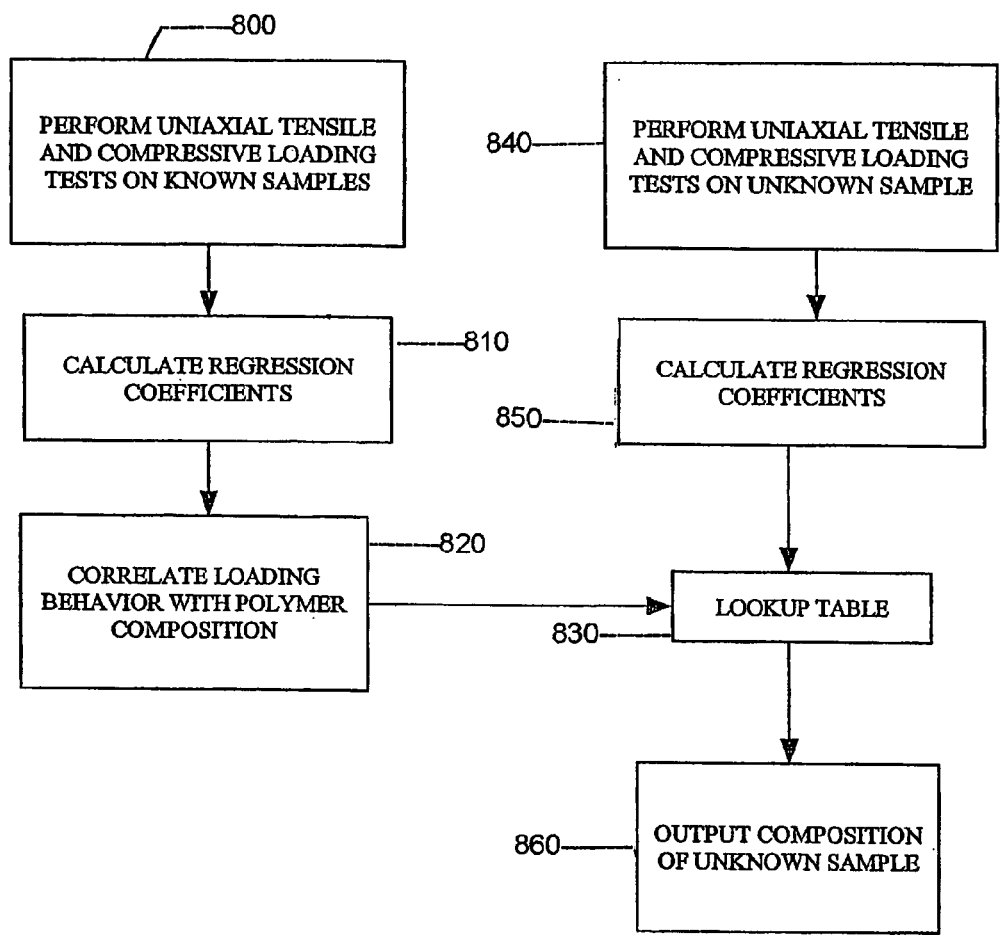
FIG. 8 is a flow chart illustrating a method to establish a mathematical correlation between known samples and a training set of loading data in order to permit the predicting of micro-structure and composition of an unknown sample by macro-level testing and comparison with the mathematical correlation.

With reference now to FIG. 8 and continuing reference to FIGS. 1–7, in accordance with another embodiment of the present invention, a method of predicting the microstructure, and therefore, chemical composition of an unknown sample is illustrated. The method includes performing one or more tensile and/or compressive uniaxial loading tests on known samples at step 800. As discussed above, each uniaxial loading test on a known sample provides uniaxial loading data, preferably in terms of stress vs. strain (illustrated, for example, in FIGS. 2–5). For each set of uniaxial loading data, a set of regression coefficients are calculated at step 810. More particularly, each plot of stress vs. strain is fit with a stress-strain function of the form provided in equation (5) and regression coefficients A, B, C, a, b, and c are calculated.

As steps 800 and 810 are repeated for a set of known compositions, the respective uniaxial loading behavior, and therefore respective regression coefficients, are correlated with each corresponding known polymer composition at step 820. Each correlation may be represented and/or stored in terms of a correlation plot, a correlation function, and/or a lookup table (shown at step 830).

The method continues at step 840 where one or more tensile and/or compressive uniaxial loading tests are performed on an unknown sample in the manner described more fully above. The stress-strain data collected from each uniaxial loading test is fit with a stress-strain function of the form provided in equation (5) and a plurality of regression coefficients are calculated at step 850. These regression coefficients are compared to those of the known compositions stored in the lookup table 830. Provided that an adequate correlation exists between the regression coefficients of the unknown sample and at least one set of the regression coefficients within the lookup table, the composition of the unknown sample is determined at step 860 without any invasive or otherwise destructive testing performed on the unknown sample.

Figure 9:
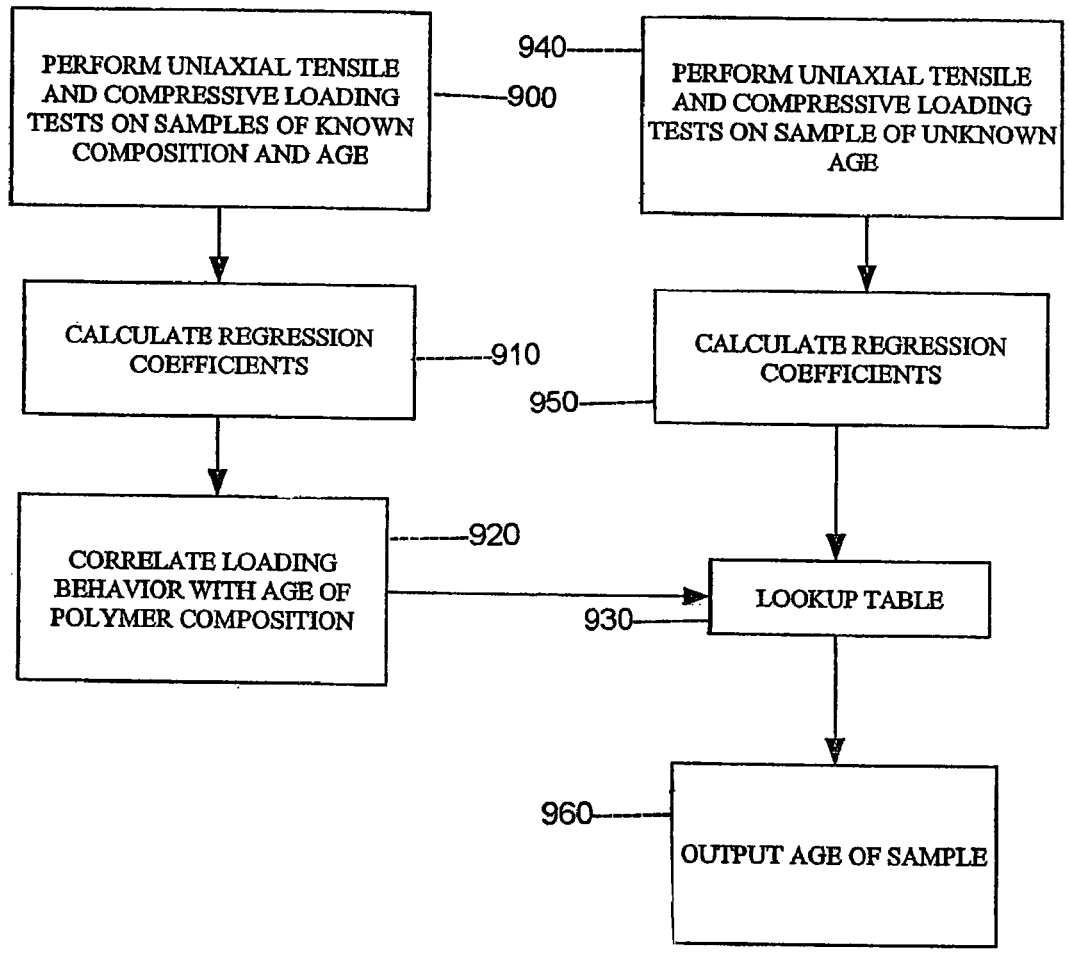
FIG. 9 is a flow chart illustrating a method to establish a mathematical correlation between known samples of different ages and a training set of loading data in order to permit the predicting of the age of a known composition by macro-level testing and comparison with mathematical correlation.

With reference to FIG. 9 and continuing reference to FIG. 8, in accordance with another embodiment of the present invention, a method of predicting the age of a composition based on macro-level tests is provided. The method includes performing one or more tensile and/or compressive uniaxial loading tests on samples of a known composition at different ages at step 900. In other words, step 900 includes developing a training set for the aging of a known composition. Each uniaxial loading test on a known sample provides uniaxial loading data, preferably in terms of stress vs. strain (illustrated, for example, in FIGS. 2–5). As discussed above, for each set of uniaxial loading data, a plurality of regression coefficients are calculated at step 910. More particularly, each plot of stress vs. strain is fit with a stress-strain function of the form provided in equation (5) and regression coefficients A, B, C, a, b, and c are calculated.

As steps 900 and 910 are repeated for a known composition at a plurality of known ages, the respective uniaxial loading behavior and therefore respective regression coefficients, are correlated with each corresponding age of the known polymer composition at step 920. Each correlation may be represented and/or stored in terms of a correlation plot, a correlation function, and/or a lookup table (shown at step 930).

The method continues at step 940 where one or more tensile and/or compressive uniaxial loading tests are performed on a sample of known composition, but unknown age, in the manner described more fully above. The stress-strain data collected from each uniaxial loading test is fit with a stress-strain function of the form provided in equation (5) and a plurality of regression coefficients are calculated at step 950. These regression coefficients are compared to those stored in the lookup table 930. Provided that an adequate correlation exists between the regression coefficients of the sample of unknown age and at least one set of the regression coefficients within the lookup table, the age of the unknown sample is determined at step 960 without any invasive or otherwise destructive testing performed on the unknown sample.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

I claim:
1. A method of determining internal structural features of a hyperelastic material, said method comprising:
(a) performing at least one uniaxial loading test on a sample comprised of the hyperelastic material, said uniaxial loading test yielding uniaxial loading data;
(b) filling the uniaxial loading data with a stress-strain function of the form:

$$\sigma = \lambda \frac{A\lambda^2 + B\lambda + C}{a\lambda^2 + b\lambda + c}$$

where $\sigma$ is a measure of the uniaxial loading on the sample, A is a measure of the strain on the sample, and A, B, C, a, b, and c are coefficients relating the stress-strain function to the uniaxial loading data;
(c) determining values for the coefficients A, B, C, a, b, c;

(d) computing a plurality of statistical parameters α, β, γ, $\alpha_1$, $\beta_1$, and $\gamma_1$ using equations of the form:

$$\sigma = \alpha + \beta \tan(\gamma\psi) \text{ and } \lambda = \alpha_1 + \beta_1 \tan(\gamma_1\phi);$$

(e) determining a set of internal structural features of the hyperelastic material from the statistical parameters, said internal structural features including at least one of (i) molecular chain length, (ii) molecular segment orientations and lengths, (iii) cross-link density, (iv) material density, (v) molecular orientation, (vi) molecular shape, (vii) type of randomness, and (viii) specific distribution of monomer content; and (f) storing said parameters.

2. The method as set forth in claim 1, wherein step (a) includes:
performing a set of uniaxial tensile loading tests on the sample; and
performing a set of uniaxial compressive loading tests on the sample.

3. The method as set forth in claim 1, wherein step (c) includes:
performing a curve fit analysis using the uniaxial loading data and the stress-strain function.

4. A method of determining performance characteristics of a polymer part having a given composition, said method comprising:
(a) performing at least one macro-level loading experiment on a sample comprised of the given composition;
(b) from the macro-level loading experiment, determining a plurality of internal structural features, said internal structural features being characterized by a plurality of coefficients A, B, C, a, b, and c;
(c) performing a finite element analysis using (i) the set of coefficients A, B, C, a, b, and c; and (ii) a set of geometric configuration coefficients corresponding to the structure of the polymer part;
and (d) storing said performance characteristics.

5. The method as set forth in claim 4, wherein step (a) includes:
performing a set of uniaxial tensile loading tests on the sample to yield uniaxial tensile loading data; and
performing a set of uniaxial compressive loading tests on the sample to yield uniaxial compressive loading data.

6. The method as set forth in claim 5, wherein step (b) includes:
fitting the uniaxial tensile and compressive loading data with a stress-strain function including a ratio of two polynomials.

7. The method as set forth in claim 6, wherein the stress-strain function is of the form:

$$\sigma = \lambda \frac{A\lambda^2 + B\lambda + C}{a\lambda^2 + b\lambda + c}$$

where σ is a measure of at least one of the tensile and compressive uniaxial loading on the sample, and λ is a measure of the strain of the sample.

8. The method as set forth in claim 7, wherein step (b) further includes:
performing a curve fit analysis using at least one of the tensile and compressive uniaxial loading data and the stress-strain function to determine A, B, C, a, b, and c.

9. A method of designing a polymer part having desired performance characteristics, said method comprising:

(a) collecting uniaxial loading data from a polymer sample having a first composition;

(b) fitting the uniaxial loading data with a stress-strain function having the form:

$$\sigma = \lambda \frac{A\lambda^2 + B\lambda + C}{a\lambda^2 + b\lambda + c}$$

where σ is a measure of the uniaxial loading on the sample, λ is a measure of the strain on the sample, and A, B, C, a, b, c are coefficients relating the stress-strain function to the uniaxial loading data;

(c) determining values for the coefficients A, B, C, a, b, c;

(d) computing a set of statistical parameters based on the coefficients A, B, C, a, b, c, said statistical parameters being related to internal structural features of the polymer sample from which the uniaxial loading data is collected;

(e) modifying at least one of the statistical parameters, said modified statistical parameters corresponding to a second polymer composition;

(f) calculating a plurality of coefficients A', B', C', a', b', and c' corresponding to the second polymer composition, said calculation being based on the modified statistical parameters; and (g) performing a computer-simulated structural analysis on a simulation of the polymer part having the second polymer composition to test performance characteristics; and (h) storing parameters.

10. The method as set forth in claim 9, further comprising:
(i) in response to step (g), determining whether the polymer part exhibits the desired performance characteristics.

11. The method as set forth in claim 10, further comprising:
(j) in response to step (i), if the polymer part exhibits undesired performance characteristics, modifying at least one of the statistical parameters in order to impose a third polymer composition; and
(k) repeating steps (f)–(h) based on the third polymer composition.

12. The method as set forth in claim 10, wherein step (d) includes: computing a set of statistical parameters α, β, γ, $\alpha_1$, $\beta_1$, and $\gamma_1$ using equations of the form:

$$\sigma = \alpha + \beta \tan(\gamma\psi) \text{ and } \lambda = \alpha_1 + \beta_1 \tan(\gamma_1\phi),$$

wherein said statistical parameters are related to a plurality of internal structural features including at least one of (i) molecular chain length, (ii) molecular segment orientations and lengths, (iii) cross-link density, (iv) material density, (v) molecular orientation, (vi) molecular shape, (vii) type of randomness, and (viii) specific distribution of monomer content.

13. The method as set forth in claim 10, wherein step (c) includes:
performing a curve fit analysis using the uniaxial loading data and the stress-strain function.

14. The method as set forth in claim 10, wherein step (a) includes:
measuring strain on the polymer sample as a function of tensile stress; and
measuring strain on the polymer sample as a function of compressive stress.

15. The method as set forth in claim 10, wherein the computer-simulated structural analysis comprises:
a finite element structural analysis.

16. A system for characterizing rheology of rubber-like materials, said system including:
means for collecting uniaxial loading data from a sample;
means for fitting the uniaxial loading data with a stress-strain function which includes a ratio of two polynomials;
means for determining values for a set of coefficients associated with the stress-strain function;
means for computing a set of statistical parameters from the plurality of determined coefficients;
means for deriving the internal structural properties of the rubber-like material from the computed statistical parameters, said internal structural properties including at least one of (i) molecular chain length, (ii) molecular segment orientations and lengths, (iii) cross-link density, (iv) material density, (v) molecular orientation, (vi) molecular shape, (vii) type of randomness, and (viii) specific distribution of monomer content; and
means for storing said coefficients.

17. The system according to claim 16, wherein the stress-strain function is a function of the form:

$$\sigma = \lambda \frac{A\lambda^2 + B\lambda + C}{a\lambda^2 + b\lambda + c}$$

where $\sigma$ is the measure of the uniaxial loading on the sample, $\lambda$ is a measure of the strain of the sample, and A, B, C, a, b, and c are coefficients relating relating the stress-strain function to the uniaxial loading data.

18. A non-invasive method for predicting a chemical composition of an unknown sample, said method comprising:
(a) collecting deformation data from a plurality of samples of known chemical composition;
(b) for each sample of known chemical composition, correlating the collected deformation data with the corresponding chemical composition;
(c) collecting deformation data from a sample of unknown chemical composition;
(d) comparing the deformation data from the sample of unknown composition with the deformation data from the samples of known composition; and
(e) storing said data.

19. The method as set forth in claim 18 further including:
for each sample of known chemical composition, calculating a set of regression coefficients corresponding to the collected deformation data; and
for the sample of unknown chemical composition, calculating a set of regression coefficients corresponding to the collected deformation data.

20. The method as set forth in claim 19, wherein the steps of calculating a set of regression coefficients comprises:
fitting the deformation data with a stress-strain function of the form:

$$\sigma = \lambda \frac{A\lambda^2 + B\lambda + C}{a\lambda^2 + b\lambda + c}$$

where $\sigma$ is a measure of the deformation on the sample, $\lambda$ is a measure of the strain on the sample, and A, B, C, a, b, and c are the regression coefficients.

21. The method as set forth in claim 20, wherein step (d) includes:
comparing the regression coefficients corresponding to the sample of unknown chemical composition to the regression coefficients corresponding to the samples of known chemical composition.

22. A method for determining performance characteristics of a tire rubber comprising:
(a) performing at least one uniaxial loading test on a sample comprised of the hyperelastic material, said uniaxial loading test yielding uniaxial loading data;
(b) fitting the uniaxial loading data with a stress-strain function of the form:

$$\sigma = \lambda \frac{A\lambda^2 + B\lambda + C}{a\lambda^2 + b\lambda + c}$$

where $\sigma$ is a measure of the uniaxial loading on the sample, h is a measure of the strain on the sample, and A, B, C, a, b, and c are coefficients relating the stress-strain function to the uniaxial loading data;
(c) determining values for the coefficients A, B, C, a, b, c;
(d) computing a plurality of statistical parameters or Y, ú, $\epsilon$, $Y_1$, and $ú_1$, $\epsilon_1$ using equations of the form:

$\sigma = \alpha + \beta \tan(\gamma_1 \psi)$ and $\lambda = \alpha_1 + \beta_1 \tan(\gamma_1 \phi)$;

(e) determining a set of internal structural features of the hyperelastic material from the statistical parameters, said internal structural features including at least one of (i) molecular chain length, (ii) molecular segment orientations and lengths, (iii) cross-link density, (iv) material density, (v) molecular orientation, (vi) molecular shape, (vii) type of randomness, and (viii) specific distribution of monomer content; and
(f) storing said parameters.

* * * * *